United States Patent [19]

Skaletzky

[11] 4,377,586

[45] Mar. 22, 1983

[54] DIURETIC 2,6-DIARYL-4-PYRIDINE CARBOXYLIC ACIDS

[75] Inventor: Louis L. Skaletzky, Parchment, Mich.

[73] Assignee: The Upjohn Company, Kalamazoo, Mich.

[21] Appl. No.: 259,135

[22] Filed: Apr. 30, 1981

[51] Int. Cl.$^3$ .................. A61K 31/44; C07D 213/55
[52] U.S. Cl. .................................. 424/266; 546/326
[58] Field of Search ................... 546/326; 424/266

[56] References Cited

U.S. PATENT DOCUMENTS

| | | | |
|---|---|---|---|
| 3,600,396 | 8/1971 | Ash et al. | 546/334 |
| 3,753,997 | 8/1973 | Ash et al. | 546/194 |
| 3,763,148 | 10/1973 | Ash et al. | 546/326 |
| 3,764,604 | 10/1973 | Ash et al. | 546/133 |

*Primary Examiner*—Alan L. Rotman
*Attorney, Agent, or Firm*—Lawrence T. Welch

[57] ABSTRACT

The present invention provides a novel method of inducing diuresis by administering certain 2,6-diaryl-4-pyridinecarboxylic acid derivatives. Also provided are novel compounds and pharmaceutical compositions to be used in this method.

3 Claims, No Drawings

DIURETIC 2,6-DIARYL-4-PYRIDINE CARBOXYLIC ACIDS

DESCRIPTION

BACKGROUND OF THE INVENTION

The present invention relates to a novel method of inducing diuresis in mammals. This invention further provides novel compounds to be used in this method. In particular, the present invention relates to the use of certain 2,6-diaryl-4-pyridinecarboxylic acids as diuretics.

Diuretics are agents which increase the rate of urine formation. In particular, they increase net renal excretion of solute (e.g., electrolytes such as sodium, potassium, chloride, and bicarbonate ions) and water. They are useful for a variety of pharmacological purposes. The most important such purposes is the treatment of edema, i.e., the presence of excess fluid in the intercellular tissue spaces of the body. Diuretics are also useful in the treatment of certain types of hypertension.

In a healthy individual, a relatively constant volume of extracellular fluid is maintained. Thus, sodium and water excretion by the kidney is adjusted according to the variations in salt and water intake. In certain disease states, however, the rate of excretion of sodium and water may be so reduced that even a small daily intake of sodium and water is retained and this leads to a progressive expansion of the volume of extracellular fluid. Disease states which cause the rate of excretion of sodium and water to be reduced include congestive heart failure, cirrhosis of the liver, and various renal diseases. As a rule, untreated edematous states are characterized by expansion of extracellular fluid volume without distortion of the composition of that fluid.

Thus, since the goal of diuretic therapy is the mobilization of edematous fluid in such a manner that the extracellular fluid is restored toward normal, in terms of both volume and composition, it would be advantageous to employ diuretic agents which have little or no effect on electrolyte concentrations.

A number of diuretic agents are known. These include mercurial diuretics, thiazide diuretics, "loop" diuretics, osmotic diuretics, and carbonic anhydrase inhibitors. Other diuretics include furosemide, ethacrynic acid, spironolactone, and triamterene. See Goth Medical Pharmacology, 9th Edition (1978), and Goodman and Gillman, The Pharmacological Basis of Therapeutics, 5th Edition (1971).

One problem with the prior art diuretic agents is that generally the more potent the diuretic, the more it tends to distort the electrolyte composition of the extracellular fluid. Spironolactone and triamterene conserve potassium, but they are not very potent when used alone. The mercurial diuretics also do not greatly effect the potassium balance, but they must be administered intramuscularly. Mercurial dicuretics have many undesirable side effects. They can cause an accumulation of mercury, which is highly toxic.

The 2,6-diaryl-pyridinecarboxylic acids of the present invention are trivially named as bis-aryl-isonicotinic acids. Some of the isonicotinic acids of the present invention are known and have been disclosed as useful as intermediates in the production of anti-malarial compounds. See M. P. LaMontagne, et al., J. Med. Chem. 16:1040-1041 (1973); P. Blumbergs et al., J. Med. Chem. 15:808-812 (1972); A. Markovac, J. Med. Chem. 15:918-922 (1972); and U.S. Pat. Nos. 3,753,997; 3,763,148; and 3,600,396.

The compounds employed in the method of the present invention are derivatives of 2,6-diphenylisonicotinic acid, which has the chemical structure and numbering as shown in Formula I. This compound is named 2,6-diphenyl-4-pyridinecarboxylic acid using the Chemical Abstracts numbering system. (See Naming and Indexing of Chemical Substances for Chemical Abstracts During the 9th Collective Period, a reprint of Section 4 from the Chemical Abstracts Vol. 76 Index Guide (1972-1976).)

PRIOR ART

Many classes of diuretics are known. See, e.g., Goth, Med. Pharma. 9th Ed. (1978); and Goodman and Gillman, The Pharmacological Basis of Therapeutics, 5th ed. (1971). 2,6-Diaryl-4-pyridinecarboxylic acids are disclosed as intermediates for anti-malarial compounds in U.S. Pat. Nos. 3,753,997; 3,763,148; and 3,600,396 and J. Med. Chem., 15:918-922 (1972); J. Med. Chem. 16:1040-1041 (1973); and J. Med. Chem., 15:808-812 (1972)

SUMMARY OF THE INVENTION

The present invention provides a method for inducing diuresis in a human which comprises administering to said human an amount effective to cause diuresis of a compound of the Formula II, wherein
(1) $R_{10}$ is hydrogen or methyl;
(2) $R_{20}$ is hydrogen or a pharmacologically acceptable cation;
(3) $X_{10}$ is hydrogen or trifluoromethyl;
(4) $X_{20}$ is hydrogen, chloro, fluoro, bromo, iodo, methyl, or trifluoromethyl;
(5) $X_{30}$ is hydrogen, methyl, chloro, bromo, iodo, trifluoromethyl, phenyl, p-fluorophenyl, phenoxy, p-fluorophenoxy, thiophenoxy, or —$CH_2$—$R_{50}$, wherein $R_{50}$ is ($C_2$–$C_7$) alkyl;
(6) $X_{40}$ is hydrogen, chloro, fluoro, trifluoromethyl, or methyl, or
(7) $X_{30}$ and $X_{40}$ when taken together with the phenyl moiety to which they are attached form 2-naphthalenyl, 5,6,7,8-tetrahydro-2-naphthalenyl, or 6-chloro-2-naphthalenyl;
(8) $X_{50}$ is hydrogen, ($C_1$–$C_4$) alkoxy or acetoxy; and
with the following provisos:
  (a) at least one of $X_{10}$ and $X_{20}$ and at least one of $X_{30}$ and $X_{40}$ is other than hydrogen;
  (b) $X_{10}$ is trifluoromethyl only when $X_{20}$ is hydrogen, $X_{30}$ is hydrogen, and $X_{40}$ is trifluoromethyl;
  (c) $X_{40}$ is chloro only when $X_{30}$ is chloro;
  (d) one of $X_{30}$ and $X_{40}$ is methyl only when the other is methyl;
  (e) $X_{20}$ is methyl only when $X_{30}$ and $X_{40}$ form 2-naphthalenyl;
  (f) $X_{50}$ is ($C_1$–$C_4$) alkoxy or acetoxy only when $X_{10}$ and $X_{40}$ are hydrogen, $X_{20}$ is chloro, bromo, iodo, or trifluoromethyl, and $X_{30}$ is chloro, bromo, iodo, trifluoromethyl, or $CH_2$—$R_{50}$;
  (g) $X_{20}$ is fluoro only when $R_{10}$ is methyl and $X_{30}$ is chloro;
  (h) $X_{30}$ is thiophenoxy only when $X_{10}$, $X_{40}$, and $X_{50}$ are hydrogen; and
  (i) $X_{40}$ is fluoro only when $X_{30}$ is phenyl.

This invention also provides a compound of the Formula III, wherein
(1) $R_{10}$ is hydrogen or methyl;

(2) $R_{20}$ is hydrogen or a pharmacologically acceptable cation;

(3) $X_{21}$ is chloro, fluoro, bromo, iodo, methyl, or trifluoromethyl;

(4) $X_{31}$ is hydrogen, methyl, chloro, bromo, iodo, trifluoromethyl, phenyl, p-fluorophenyl, phenoxy, p-fluorophenoxy, thiophenoxy, or —$CH_2R_{50}$ wherein $R_{50}$ is ($C_2$–$C_7$) alkyl;

(5) $X_{41}$ is hydrogen, chloro, fluoro, trifluoromethyl, or methyl; or (6) $X_{31}$ and $X_{41}$ when taken together with the phenyl moiety to which they are attached form 2-naphthalenyl or 5,6,7,8-tetrahydro-2-naphthalenyl, or 6-chloro-2-naphthalenyl;

(7) $X_{50}$ is hydrogen, ($C_1$–$C_4$) alkoxy or acetoxy; and with the following provisos:

(a) at least one of $X_{31}$ and $X_{41}$ is other than hydrogen;

(b) one of $X_{31}$ and $X_{41}$ is methyl only when the other is methyl;

(c) $X_{21}$ and $X_{31}$ are chloro, bromo, or trifluoromethyl (being the same or different) only when $R_{10}$ or $X_{50}$ is other than hydrogen;

(d) $X_{21}$ is chloro only when $X_{41}$ is not chloro;

(e) $X_{21}$ is methyl only when $X_{31}$ and $X_{41}$ form 2-naphthalenyl;

(f) $X_{50}$ is ($C_1$–$C_4$) alkoxy or acetoxy only when $X_{41}$ is hydrogen, $X_{21}$ is chloro, bromo, iodo, or trifluoromethyl, $X_{31}$ is chloro, bromo, iodo, trifluoromethyl, or $CH_2R_{50}$;

(g) $X_{21}$ is fluoro only when $R_{10}$ is methyl and $X_{31}$ is chloro;

(h) $X_{31}$ is thiophenoxy only when $X_{41}$ and $X_{50}$ are hydrogen; and (i) $X_{41}$ is fluoro only when $X_{31}$ is phenyl.

This invention also provides:

(1) a pharmaceutical composition comprising
  (a) a compound of the formula II, wherein all variables are defined as given above; and
  (b) a pharmaceutical excipient;

(2) A method for producing an antihypertensive effect in a human which comprises concomittantly administering to said human
  (a) an amount effective to induce diuresis of a compound of the formula II, wherein all variables are defined as given above; and
  (b) an antihypertensive agent; and (3) A pharmaceutical composition comprising:
  (a) a compound of the formula II, wherein all variables are as defined above;
  (b) an antihypertensive agent; and
  (c) a pharmaceutical excipient.

The compounds of the present invention are administered orally or parenterally, (e.g., intravenously, intraperitoneally, or intramuscularly). The preferred route of administration is oral.

An amount effective to induce diuresis of the compounds of the present invention when administered orally is typically from 0.01 to 30 mg per kg daily, administered in a single dose or from 2 to 4 times daily. When other routes of administration are used, equivalent dosages are employed.

The dosage regimen for inducing diuresis using the method of the present invention is selected in accordance with a variety of factors, including the type, age, weight, sex, and medical condition of the mammal, the severity of the condition being treated, and the particular compound employed. An ordinarily skilled physician will readily determine and prescribe the correct amount of the compound to induce the desired level of diuretic response. In so proceeding, the physician could employ relatively low dosages at first, assessing the patient's response, subsequently increasing the dose until the maximum desired response is obtained. For example when diuresis is employed in treating moderate hypertension (diastolic pressure less than 100 mm of mercury) relatively low doses may prove fully effective, while severely hypertensive patients will ordinarily require larger doses to achieve a correspondingly greater antihypertensive effect.

When the compounds of the present invention are administered orally, they are formulated as tablets, capsules, or as liquid preparations, with the usual pharmaceutical carriers, binders, and the like. For parenteral administration, pharmaceutically acceptable sterile suspensions or solutions are preferred.

The compounds of the present invention may also be administered rectally or vaginally in forms such as suppositories or bougies.

The compounds of the present invention may be combined with other diuretics such as hydrochlorothiazide, trichloromethiazide, furosemide, ethoxzolamide, chlorthalidone, triamterene, spironolactone, and the like. They may also be combined with anti-hypertensive agents such as reserpine, deserpidine, hydralazine hydrochloride, mecamylamine hydrochloride, guanethidine sulfate, methyldopa, pentaerythritol tetranitrate, minoxidil, clonidine, prazosin, propranolol, angiotensin I converting enzyme inhibitor, and the like. They may also be combined with sedatives and tranquilizers such as butobarbital, amobarbital, phenobarbital, chlordiazepoxide hydrochloride, chlorpromazine, thioridazine, meprobamate, haloperidol, triazolam, alprazolam, diazepam and the like.

An ordinarily skilled physician will readily determine the necessity of employing a diuretic agent such as the compounds disclosed herein with the other diuretics, anti-hypertensive agents, sedatives and tranquilizers, based upon the patient's particular medical needs and the condition being treated.

It has been suprisingly and unexpectedly found that the compounds of the present invention represent potent oral diuretics which virtually do not distort the electrolyte balance of extracellular fluid.

The compounds of the present invention induce diuresis in rats by oral administration. By measuring the volume and electrolyte concentration of the urine of rats dosed orally with the compounds of the present invention versus the volume and electrolyte concentration of the urine of untreated control rats, the compounds of the present invention exhibit a greatly increased excretion of: (1) fluid volume, (2) sodium ions and (3) chloride ions, while the total amount of potassium excretion remains virtually unchanged. Thus the method and compounds of the present invention represents a surprisingly and unexpectedly potent and efficacious means of inducing diuresis and natriuresis (sodium ion excretion) without the kaliuretic (potassium ion excreting) side effect of other oral diuretic methods. Because of the diuretic and natriuretic activity in the absence of kaliuretic activity the compounds of this invention do not distort electrolyte concentration or composition of body fluids.

The compounds of the present invention are prepared by the process as depicted in Chart A. $X_{10}$, $X_{20}$, $X_{30}$, $X_{40}$, $X_{50}$, and $R_{10}$ are defined as above. $R_{60}$ is hydrogen or alkyl of one to four carbon atoms. This process is essentially the process disclosed in J. Med. Chem. 15:808 (1972) and J. Med. Chem. 15:918 (1972). A pyridinium salt of the Formula X is reacted with an aroyl acrylic acid or ester of the Formula XI in the presence of ammonium acetate in a suitable solvent such as methanol to yield a compound of the Formula XII. When an ester of the Formula XI is used as the starting material, the ester moiety is removed by well known means to yield the Formula XII acid. The Formula XII acid may be purified by forming the corresponding ester, purifying the ester by conventional means (e.g., chromatography or crystallization), saponifying the ester, and recrystallizing the acid. Formula XII includes all of the Formula II acids within its scope, and as well as all of the Formula III acids. When $R_{10}$ is methyl, $R_{60}$ is other than hydrogen. Pharmacologically acceptable salts are prepared by well known means. The pyridinium salts and aroyl acrylic acids are prepared from readily available acetophenones by the methods disclosed in the references cited above.

The carbon atom content of various hydrocarbon-containing moieties is indicated by a prefix designating the minimum and maximum number of carbon atoms in the moiety, i.e., the prefix $(C_i-C_j)$ indicates a moiety of the integer "i" to the integer "j" carbon atoms, inclusive. Thus $(C_1-C_3)$alkyl refers to alkyl of one to 3 carbon atoms, inclusive, or methyl, ethyl, propyl, and isopropyl.

Examples of alkyl of from 2 to 7 carbon atoms includes ethyl, propyl, butyl, pentyl, hexyl, heptyl, and isomeric forms thereof. Examples of alkoxy of from one to 4 carbon atoms include methoxy, ethoxy, propoxy, butoxy, and isomeric forms thereof.

Pharmacologically acceptable cations of the present invention include the pharmacologically acceptable metal cations, ammonium, amine cations, or quaternary ammonium cations.

Especially preferred metal cations are those derived from the alkali metals, e.g., lithium, sodium, and potassium; and from the alkaline earth metals, e.g., magnesium and calcium, although cationic forms of other metals, e.g., aluminum, zinc, and iron are within the scope of this invention.

Pharmacologically acceptable amine cations are those derived from primary, secondary, or tertiary amines. Examples of suitable amines are methylamine, dimethylamine, trimethylamine, ethylamine, dibutylamine, triisopropylamine, N-methylhexylamine, decylamine, dodecylamine, allylamine, crotylamine, cyclopentylamine, dicyclohexylamine, benzylamine, dibenzylamine, α-phenylethylamine, β-phenylethylamine, ethylenediamine, diethylenetriamine, and the like aliphatic, cycloaliphatic, araliphatic amines containing up to and including about 18 carbon atoms, as well as heterocyclic amines, e.g., piperidine, morpholine, pyrrolidine, piperazine, and lower-alkyl derivatives thereof, e.g., 1-methylpiperidine, 4-ethylmorpholine, 1-isopropylpyrrolidine, 2-methylpyrrolidine, 1,4-dimethylpiperazine, 2-methylpiperidine, and the like, as well as amines containing water-solubilizing or hydrophilic groups, e.g., mono-, di-, and triethanolamine, ethyldiethanolamine, N-butylethanolamine, 2-amino-2-ethyl-1,3-butylethanolamine, 2-amino-1-butanol, 2-amino-2-ethyl-1,3-propanediol, 2-amino-2-methyl-1-propanol, tris(hydroxymethyl)aminomethane, N-phenylethanolamine, N-(p-tert-amylphenyl)-diethanolamine, glactamine, N-methylglycamine, N-methylglucosamine, ephedrine, phenylephrine, epinephrine, procaine, and the like.

Examples of suitable pharmacologically acceptable quaternary ammonium cations are tetramethylammonium, tetraethylammonium, benzyltrimethylammonium, phenyltriethylammonium, and the like.

The diuretic compounds of the present invention may be formulated into pharmaceutical compositions, employing a pharmaceutically acceptable carrier.

The pharmaceutical forms contemplated by this invention include pharmaceutical compositions suitable for oral, parenteral, vaginal, and rectal use, e.g., tablets, powder packets, cachets, dragees, capsules, solutions, suspensions, sterile injectable forms, suppositories, bougies, and the like. Suitable diluents or carriers such as carbohydrates (lactose), proteins, lipids, calcium phosphate, cornstarch, stearic acid, methylcellulose and the like may be used as carriers or for coating purposes. Oil, e.g., coconut oil, sesame oil, safflower oil, cottonseed oil, peanut oil may be used for preparing solutions or suspensions of the active drug. Sweetening, coloring and flavoring agents may be added. By "pharmaceutical excipient" is meant any of these and similar well known forms of drug formulations.

When used in conjunction with antihypertensive therapy, the compounds may be formulated with antihypertensive agents by means well known in the art, employing a pharmaceutical excipient as defined above.

2,6-bis(4-Chlorophenyl)-4-pyridinecarboxylic acid is the most preferred compound for use in the methods of this invention.

DESCRIPTION OF THE PREFERRED EMBODIMENTS

The novel compounds of the present invention are all prepared by the procedures illustrated by the Examples given below.

EXAMPLE 1

2-(4-chlorophenyl)-6-[3-(trifluoromethyl)phenyl]-4-pyridinecarboxylic acid (Formula III: $X_{21}$ is chloro, $X_{41}$ is trifluoromethyl, and $X_{31}$, $X_{50}$, $R_{10}$ and $R_{20}$ are hydrogen)

A mixture of 3.5 g (0.01 mole) of m-trifluoromethylphenacylpyridinium bromide, 2.1 g (0.01 mole) of p-chlorobenzoylacrylic acid and 6 g of ammonium acetate and 10 ml of glacial acetic acid and 1 ml of acetic anhydride is heated at 120°–130° C. for 4 hr. The reaction mixture is cooled and diluted with 35 ml of water. The solid is then collected and partitioned between 150 ml of 2% potassium carbonate and chloroform. The aqueous layer is extracted with chloroform and then ether. This aqueous layer is concentrated and treated with acetic acid to yield a gummy solid which is triturated with ether. This solid is then collected and recrystallized from ethanol-water to yield 1.3 g (34.4%) of the titled solid with a melting point of 222° C. The C:H:N:Cl ratio is 60.69:3.03:3.79:9.42.

EXAMPLE 2

2-(4-bromophenyl)-6-[3-(trifluoromethyl)phenyl]-4-pyridinecarboxylic acid (Formula III: $X_{21}$ is bromo, $X_{41}$ is trifluoromethyl, $X_{31}$, $X_{50}$, $R_{10}$ and $R_{20}$ are hydrogen)

A mixture of 2.0 g (0.0079 mole) of p-bromobenzoylacrylic acid, 2.75 g (0.0079 mole) of m-trifluoromethylphenacylpyridinium bromide and 5 g of ammonium acetate and 25 ml of methanol and 2.5 ml of glacial acetic acid is stirred at reflux for 6 hr. The mixture is concentrated in vacuo and the residue is treated with 50% acetic acid-water to give a solid which is recrystallized from ethanol yielding 1.35 g (40%) of the titled crystals having a melting point of 233°–234° C. The C:H:N ratio is 54.40:2.57:3.21.

EXAMPLE 3

2-[1,1'-biphenyl]-4-yl-6-(4-chlorophenyl)-4-pyridinecarboxylic acid (Formula III: $X_{21}$ is chloro, $X_{31}$ is phenyl, $X_{41}$, $X_{50}$, $R_{10}$, and $R_{20}$ are hydrogen)

A mixture of 3.54 g (0.01 mole) of the pyridinium salt corresponding to the titled product, 2.11 g (0.01 mole) of p-chlorobenzoylacrylic acid and 8.5 g of ammonium acetate in 20 ml of methanol is stirred at reflux for 6 hr. The solid is collected and recrystallized from acetic acid-water. The yield is 3.3 g (85.5%) of the titled crystals with a melting point of 258°–260° C. The C:H:N ratio is 73.45:4.10:3.80.

EXAMPLE 4

2-(4-chlorophenyl)-6-(2-naphthalenyl)-4-pyridinecarboxylic acid (Formula III: $X_{21}$ is chloro, $X_{31}$ and $X_{41}$ form 2-naphthalenyl, $X_{50}$, $R_{10}$ and $R_{20}$ are hydrogen)

A mixture of 3.3 g (0.01 mole) of the pyridinium salt corresponding to the titled product, 2.1 g (0.01 mole) of p-chlorobenzoylacrylic acid, 5.8 g of ammonium acetate and 10 ml of methanol, 10 ml of glacial acetic acid, and 1.2 ml of acetic anhydride is stirred at reflux for 1.5 hr. The reaction is cooled and the solid is collected. The solid is then washed with cold methanol and recrystallized from ethyl acetate to yield 1.4 g (39%) of the titled crystals with a melting point of 274°–276° C. The C:H:N ratio is 73.23:3.73:4.10.

EXAMPLE 5

2-(4-chlorophenyl)-6-(3,4-dimethylphenyl)-4-pyridinecarboxylic acid (Formula III: $X_{21}$ is chloro, $X_{31}$ and $X_{41}$ are methyl, $X_{50}$, $R_{10}$, and $R_{20}$ are hydrogen)

A mixture of 3.06 g (0.01 mole) of the pyridinium salt corresponding to the titled product, 2.11 g (0.01 mole) of p-chlorobenzoylacrylic acid and 8.5 g of ammonium acetate in 20 ml of methanol is stirred at reflux for 6 hr. The mixture is partitioned between methylene chloride and water and the organic layer is evaporated and the residue is recrystallized from ethanol-water to yield 2.10 g (62%) of crystals having a melting point of 256°–259° C. The C:H:N ratio is 71.54:4.69:4.34.

EXAMPLE 6

2,6-bis(4-chlorophenyl)-3-methyl-4-pyridinecarboxylic acid (Formula III: $X_{21}$ and $X_{31}$ are chloro, $R_{10}$ is methyl, $X_{41}$, $X_{50}$, and $R_{20}$ are hydrogen)

A mixture of 17 g (0.10 mole) of p-chloropropiophenone and 17 g of glyoxylic acid in 20 ml of acetic anhydride containing a drop of N,N-diisopropylethylamine is heated to 135° C. An additional 2 ml of N,N-diisopropylethylamine is added and the reaction is maintained at 135° C. for three hours. The mixture is concentrated and then diluted with aqueous sodium carbonate. The mixture is then extracted with ether and the aqueous layer is acidified with hydrochloric acid and extracted with methylene chloride. The organic layer is concentrated and the residue is chromatographed on silica gel using 5% $CH_3OH$-1% acetic acid and 94% $CH_2Cl_2$. The crude β-methyl-β-(p-chlorobenzoyl)acrylic acid is dried in high vacuum yielding 11.2 g of solid. The ethyl ester is prepared by heating this crude solid and 100 ml of absolute alcohol in 3 ml of concentrated sulfuric acid for 1 hr at reflux. This mixture is concentrated, the residue is partitioned between sodium carbonate and methylene chloride. The organic layer is dried and concentrated to yield 11.9 g of oil.

A mixture of this oil, 14.7 g (0.047 mole) of the pyridinium salt corresponding to the titled product, 40 g of ammonium acetate and 100 ml of methanol is heated at reflux for 6 hr. This mixture is concentrated, diluted with water, and the solid is collected. The solid is crystallized from alcohol and chromatographed on silica gel eluting with methylene chloride to yield 9.9 g (54%) of crystals with a melting point of 87°–90° C. The product was recrystallized from ethanol to yield the ethyl ester of the titled product having a melting point 94°–95° C.

The titled product is obtained by hydrolysis of one g of the ethyl ester in warm methanol and 5 ml of 20% sodium hydroxide solution. This mixture is left at room temperature for 1.5 hr and concentrated. The residue is partitioned between ether and water. The aqueous layer is acidified and the solid is collected. The product is recrystallized from alcohol yielding 0.60 g (65%) of the titled crystals with a melting point of 236° C. The C:H:N ratio is 63.78:3.57:4.01.

EXAMPLE 7

2-(4-chlorophenyl)-6-(4-iodophenyl)-4-pyridinecarboxylic acid (Formula III: $X_{21}$ is chloro, $X_{31}$ is iodo, $X_{41}$, $X_{50}$, $R_{10}$, and $R_{20}$ are hydrogen)

A mixture of 1.7 g (0.0042 mole) of p-iodophenacylpyridinium bromide, 0.88 g (0.0042 mole) of p-chlorobenzoylacrylic acid, 2.44 g of ammonium acetate, 5 ml of methanol, 4 ml of acetic acid, and 0.4 ml of acetic anhydride is stirred at reflux for 1.25 hr. 10 ml of methanol is added and the mixture is cooled and the solid is collected. The solid is recrystallized from methanol-acetic acid-water to yield 0.90 g (49%) of the titled crystals with a melting point of 286°–287° C. The C:H:N ratio is 49.67:2.68:3.24.

EXAMPLE 8

2-(4-chlorophenyl)-6-(4-propylphenyl)-4-pyridinecarboxylic acid (Formula III: $X_{21}$ is chloro, $X_{31}$ is n-propyl, $X_{41}$, $X_{50}$, $R_{10}$, and $R_{20}$ are hydrogen)

A mixture of 3.2 g (0.01 mole) of the pyridinium salt corresponding to the titled product, 2.11 g (0.01 mole) of p-chlorobenzoylacrylic acid, and 8.5 g of ammonium acetate and 20 ml of methanol is heated at reflux for 6 hr. The mixture is diluted with water and the semi-solid is extracted into 2% potassium carbonate and ether. The ether layer is extracted with water and the aqueous layer is acidified with hydrochloric acid to precipitate a solid which is recrystallized from ethanol-water to yield 1.26 g (36%) of the titled crystals with a melting point of 226°–227° C. The C:H:N ratio is 72.07:5.40:4.06.

EXAMPLE 9

2-(4-chlorophenyl)-6-(4-phenoxyphenyl)-4-pyridinecarboxylic acid (Formula III: $X_{21}$ is chloro, $X_{31}$ is phenoxy, $X_{41}$, $X_{50}$, $R_{10}$, and $R_{20}$ are hydrogen).

A mixture of 1.85 g (0.005 mole) of the pyridinium salt corresponding to the titled product, 1.05 g (0.005 mole) of p-chlorobenzoylacrylic acid and 2.7 g of ammonium acetate in 5 ml of methanol, 5 ml of glacial acetic acid, and 0.5 ml of acetic anhydride is heated at reflux for 1.5 hr. The reaction is diluted with ice water and the precipitate is partitioned between ether and water. The ether extracts are treated with activated carbon, concentrated, and the residue recrystallized from methanol-acetic acid-water to yield 0.5 g (27.5%) of the titled crystals with the melting point of 214°–215° C. The C:H:N ratio is 71.86:4.06:3.42.

EXAMPLE 10

2-(4-chlorophenyl)-6-[4-(phenylthio)phenyl]-4-pyridinecarboxylic acid (Formula III: $X_{21}$ is chloro, $X_{31}$ is thiophenoxy, $X_{41}$, $X_{50}$, $R_{10}$, and $R_{20}$ are hydrogen)

A mixture of 3.86 g (0.01 mole) of the appropriate pyridinium salt, 2.11 g (0.01 mole) of p-chlorobenzoylacrylic acid, 5.4 g of ammonium acetate, 10 ml of methanol, 10 ml of glacial acetic acid, and 1 ml of acetic anhydride is heated at reflux for 1.5 hr. The mixture is washed and recrystallized as in Example 9 to yield 2.0 g (48%) of the titled crystals having a melting point of 213°–216° C. The C:H:N ratio is 69.01:3.95:3.37.

EXAMPLE 11

2-(4-chlorophenyl)-6-[4-(2-methylpropyl)phenyl]-4-pyridinecarboxylic acid (Formula III: $X_{21}$ is chloro, $X_{31}$ is 2-methylpropyl, $X_{41}$, $X_{50}$, $R_{10}$, and $R_{20}$ are hydrogen).

A mixture of 8.65 g (0.026 mole) of the appropriate pyridinium salt, 5.25 g (0.025 mole) of p-chlorobenzoylacrylic acid and 13.5 g of ammonium acetate in 25 ml of methanol, 25 ml of glacial acetic acid, and 5 ml of acetic anhydride is heated at reflux for 1.5 hr. The mixture is cooled, diluted with water, and partitioned between aqueous hydrochloric acid and ether. The aqueous layer is extracted with ether and the combined ether layers are treated with activated carbon, filtered, and concentrated. The residue is triturated with acetonitrile and the solid is collected and recrystallized from methanolacetic acid-water to yield 4.7 g (51%) of the titled crystals with melting point of 220°–221° C. The C:H:N ratio is 72.56:5.43:3.80.

EXAMPLE 12

2-(4-methylphenyl)-6-(2-naphthalenyl)-4-pyridinecarboxylic acid (formula III: $X_{21}$ is methyl, $X_{31}$ and $X_{41}$ form 2-naphthalenyl, $X_{41}$, $X_{50}$, $R_{10}$, and $R_{20}$ are hydrogen)

A mixture of 2.92 g (0.01 mole) of the appropriate pyridinium salt, 2.26 g (0.01 mole) of β-(2-naphthoyl)acrylic acid and 8.5 g of ammonium acetate in 20 ml of methanol is heated at reflux for 6 hr. The mixture is concentrated and the residue is diluted with water and extracted with methylene chloride. The organic layer is concentrated and the residue is chromatographed on silica gel using 5% methanol-1% acetic acid-94% methylene chloride. The product is recrystallized from ethanol yielding 1.14 g (33.6%) of the titled crystals with a melting point of 272°–274° C. The C:H:N ratio is 81.32:5.01:4.16.

EXAMPLE 13

2-(4-butylphenyl)-6-(4-chlorophenyl)-4-pyridinecarboxylic acid (Formula III: $X_{21}$ is chloro, $X_{31}$ is n-butyl, $X_{41}$, $X_{50}$, $R_{10}$, and $R_{20}$ are hydrogen)

A mixture of 8.65 g (0.026 mole) of the appropriate pyridinium salt, 5.25 g (0.025 mole) of p-chlorobenzoylacrylic acid and 13.5 g of ammonium acetate in 25 ml of methanol, 25 ml of glacial acetic acid, and 5 ml of acetic anhydride is heated at reflux for 2.5 hr. The mixture is worked up as in the preceding Examples and recrystallized from methanol:acetic acid:water to yield 2.4 g (26%) of the titled crystals with melting point of 209°–210° C. The C:H:N ratio is 72.19:5.54:3.95.

EXAMPLE 14

2-(4-chlorophenyl)-6-(5,6,7,8-tetrahydro-2-naphthalenyl)-4-pyridinecarboxylic acid (Formula III: $X_{21}$ is chloro, $X_{31}$ and $X_{41}$ form 5,6,7,8-tetrahydro-2-naphthalenyl, $X_{50}$, $R_{10}$, and $R_{20}$ are hydrogen).

A mixture of 6.6 g (0.02 mole) of the appropriate pyridinium salt, 4.2 g (0.02 mole) of p-chlorobenzoylacrylic acid and 10.8 g of ammonium acetate in 20 ml of methanol, 20 ml of glacial acetic acid, and 4 ml of acetic anhydride is heated at reflux for one hr. The mixture is cooled, the solid is collected and washed with cold methanol and recrystallized from methanol:water to yield 2.7 g (37%) of the titled crystals with a melting point of 243°–246° C. The C:H:N ratio is 72.39:5.28:3.85.

EXAMPLE 15

2-(4-chlorophenyl)-6-[4-(3-methylbutyl)phenyl]-4-pyridinecarboxylic acid (Formula III: $X_{21}$ is chloro, $X_{31}$ is 3-methylbutyl, $X_{41}$, $X_{50}$, $R_{10}$, and $R_{20}$ are hydrogen).

A mixture of 7.0 g (0.02 mole) of the appropriate pyridinium salt, 4.3 g (0.02 mole) of p-chlorobenzoylacrylic acid and 10.8 g of ammonium acetate and 20 ml of methanol, 20 ml of glacial acetic acid, and 2 ml of acetic anhydride is heated at reflux for one hr. The mixture is partitioned between ether and water. The ether layer is treated with activated carbon, concentrated and the dark gum formed is triturated with acetonitrile. The solid is collected and recrystallized from acetic acid to yield 2.85 g (37.5%) of the titled crystals with a melting point of 198°–200° C. The C:H:N:Cl ratio is 72.79:5.83:3.37:9.42.

EXAMPLE 16

2-(4-chloro-2-methoxyphenyl)-6-(4-chlorophenyl)-4-pyridinecarboxylic acid (Formula III: $X_{50}$ is methoxy, $X_{21}$ and $X_{31}$ are chloro, $X_{41}$, $R_{10}$, and $R_{20}$ are hydrogen)

The acrylic acid is prepared as described in Example 6. A mixture of 1.15 g (0.0048 mole) of the 4-chloro-2-methoxy benzoylacrylic acid, 1.5 g (0.0048 mole) of the p-chlorophenacylpyridinium salt, and 4.5 g of ammonium acetate in 10 ml of methyl alcohol is heated at reflux for 6 hr. The crude product is partitioned between methylene chloride-water. The organic layer is concentrated; residue reacted with methanol-sulfuric acid to yield the methyl ester which is purified and hydrolyzed as in Example 6 to yield 0.75 g (42%) of the titled compound with a melting point of 248–250. The C:H:N ratio is 60.69:3.59:3.67.

EXAMPLE 17

2-[2-(acetyloxy)-4-chlorophenyl]-6-(4-chlorophenyl)-4-pyridinecarboxylic acid (Formula III: $X_{50}$ is acetyloxy, $X_{21}$ and $X_{31}$ are chloro, $X_{41}$, $R_{10}$, and $R_{20}$ are hydrogen).

A mixture of 0.22 g (0.0006 mole) of 2-(4-chloro-2-hydroxyphenyl)-6-(4-chlorophenyl)-4-pyridinecarboxylic acid (prepared by reaction of the 2-methoxy compound of Example 16 with pyridine hydrochloride), 3 ml of acetic anhydride, and 0.2 g of anhydrous sodium acetate is heated at 140° for 2 hr. The mixture is cooled, diluted with water, and the solid is collected and recrystallized from chloroform-petroleum ether to yield 0.18 g (73%) of the titled compound with a melting point of 230°–231°. The C:H:N ratio is 58.24:3.25:3.32.

EXAMPLE 18

2-(4-Chlorophenyl)-6-(4'-fluoro-[1,1'-biphenyl]-4-yl)-4-pyridinecarboxylic acid (Formula III, $X_{21}$ is chloro, $X_{31}$ is p-fluorophenyl, $X_{41}$, $X_{50}$, $R_{10}$, and $R_{20}$ are hydrogen)

Following the procedure of the proceding example, the titled crystals are obtained having a melting point of 285°–286° C. and a C:H:N ratio of 70.89:3.75:2.97.

EXAMPLE 19

2-(4-Chlorophenyl)-6-(2-fluoro-[1,1'-biphenyl]-4-yl)-4-pyridinecarboxylic acid (Formula III: $X_{21}$ is chloro, $X_{31}$ is phenyl, $X_{41}$ is fluoro, $X_{50}$, $R_{10}$, and $R_{20}$ are hydrogen)

Following the procedures of the preceding examples, the titled crystals are obtained at a melting point of 271°–272° C. and a C:H:N ratio of 70.34:3.83:3.07.

EXAMPLE 20

2-(6-Chloro-2-naphthalenyl)-6-(4-chlorophenyl)-4-pyridinecarboxylic acid (Formula III: $X_{21}$ is chloro, $X_{31}$ and $X_{41}$ form 6-chloro-2-naphthalenyl, $X_{50}$, $R_{10}$, and $R_{20}$ are hydrogen)

Following the procedures of the preceding examples, the titled crystals are obtained having a melting point of 273°–274° C. and a C:H:N:Cl ratio of 66.82:3.40:3.30:18.04.

EXAMPLE 21

2-(4-Bromophenyl)-6-[4-(phenylthio)phenyl]-4-pyridine carboxylic acid (Formula III: $X_{21}$ is bromo, $X_{31}$ is thiophenoxy, $X_{41}$, $X_{50}$, $R_{10}$ and $R_{20}$ are hydrogen)

Following the procedures of the preceding examples, the titled crystals are obtained having a melting point of 219°–222° C. and C:H:N ratio of 62.56:3.68:2.71.

EXAMPLE 22

2-(4-Chlorophenyl)-6-[4-(4-fluorophenoxy)phenyl]-4-pyridinecarboxylic acid (Formula III: $X_{21}$ is chloro, $X_{31}$ is p-fluorophenoxy, $X_{41}$, $X_{50}$, $R_{10}$, and $R_{20}$ are hydrogen)

Following the procedures of the preceding examples, the titled crystals are obtained from methylene chloride:petroleum ether, having a melting point of 201°–202° C. and a C:H:N ratio of 68.70:3.77:3.68.

EXAMPLE 23

2-(4-Chlorophenyl)-6-(4-fluorophenyl)-3-methyl-4-pyridinecarboxylic acid (Formula III: $X_{21}$ is fluoro, $X_{31}$ is chloro, $R_{10}$ is methyl, $X_{41}$, $X_{50}$, and $R_{20}$ are hydrogen)

Following the procedures of the preceding examples, the titled crystals are obtained from alcohol:water, having a melting point of 239°–240° C. and a C:H:N ratio of 66.87:3.95:3.72.

EXAMPLE 24

2-[1,1'-biphenyl]-4-yl-6-(4-bromophenyl)-4-pyridine carboxylic acid (Formula III: $X_{21}$ is bromo, $X_{31}$ is phenyl, $X_{41}$, $X_{50}$, $R_{10}$, and $R_{20}$ are hydrogen)

Following the procedure of the preceding examples, the titled crystals are obtained from alcohol:water, having a melting point of 272°–274° C. and a C:H:N ratio of 66.28:4.06:2.58.

EXAMPLE 25

2-(4-Bromophenyl)-6-(2-naphthalenyl)-4-pyridinecarboxylic acid (Formula III: $X_{21}$ is bromo, $X_{31}$ and $X_{41}$ form 2-naphthalenyl, $X_{50}$, $R_{10}$ and $R_{20}$ are hydrogen)

Following the procedures of the preceding examples, the titled crystals are obtained from alcohol, having a melting point of 285°–286° C. and a C:H:N ratio of 65:49:3.52:3.21.

EXAMPLE 26

2-(4-Bromophenyl)-6-(4-chlorophenyl)-5-methyl-4-pyridine carboxylic acid (Formula III: $X_{21}$ is bromo, $X_{31}$ is chloro, $R_{10}$ is methyl, $X_{41}$, $X_{50}$, and $R_{20}$ are hydrogen)

Following the procedures of the preceding examples, the titled crystals are obtained from alcohol:water, having a melting point of 228°–230° C. and a C:H:N ratio of 56.42:3.29:3.30.

EXAMPLE 27

2,6-bis(4-Chlorophenyl)-4-pyridinecarboxylic acid (Formula II: $X_{20}$ and $X_{30}$ are chloro, $R_{10}$, $R_{20}$, $X_{10}$, $X_{40}$, and $X_{50}$ are hydrogen)

The pyridinium salt is prepared from 14 g (0.06 moles) of 2-bromo-p-chloroacetophenone and 6 ml (0.074 moles) of dry pyridine in 50 ml of absolute ethanol at reflux for 15 min. The mixture is cooled, and the salt is collected and washed with ether. The mixture is dried in vacuo to yield 18 g of the pyridinium salt.

A mixture of 12.2 g (0.039 moles) of the above solid and 8.22 g (0.039 moles) of p-chlorobenzoylacrylic acid, 23.4 g of ammonium acetate, 3.9 ml of acetic anhydride and 39 ml of acetic acid is heated at reflux (145° C.) for 4 hr. The reaction mixture is diluted with 140 ml of water, cooled to room temperature, and a brown solid is collected. This solid is suspended in 600 ml of 2% potassium carbonate. The solid is recovered and stirred with 600 ml of 2% potassium carbonate and methylene chloride for 0.5 hr. The mixture is filtered, and the aqueous layer is extracted 5 times with methylene chloride and twice with ether. The mixture is filtered once again and acidifed to pH 2 and 12 molar hydrochloric acid. The mixture is cooled, the solid is collected and washed with water, air dried, and recrystallized from alcohol, yielding 4.9 g (36.5%) of the titled crystals having a melt point of 288°–290° C. The C:H:N:Cl ratio is 62.77:3.10:4.42:20.74.

EXAMPLE 28

2,6-bis(4-Chlorophenyl)-4-pyridine carboxylic acid, sodium salt hydrate (Formula II: $X_{20}$ and $X_{30}$ are chloro, $R_{10}$, $X_{10}$, $X_{40}$, and $X_{50}$ are hydrogen, and $R_{20}$ is sodium)

A mixture of 12 g of the product of Example 28 and 1.0–1.1 equivalents of sodium hydroxide in 100 ml of water is heated and the resulting solution is filtered. The sodium salt hydrate is crystallized on cooling in an icebath to yield 11.44 g of the titled crystals, having a melting point greater than 300° C. This compound may then be lyophilized to yield solid crystals.

EXAMPLE 29

2,6-bis[3-(trifluoromethyl)phenyl]-4-pyridinecarboxylic acid) (Formula II: $X_{10}$ and $X_{40}$ are trifluoromethyl, $X_{20}$, $X_{30}$, $X_{50}$, $R_{10}$ and $R_{20}$ are hydrogen)

A mixture of m-trifluoromethyl phenacylpyridinium bromide (5.5 g, 0.016 moles), $\beta$-(3-trifluoromethylbenzoyl)acrylic acid (4.25 g, 0.017 moles), 10 g of ammonium acetate, 5 ml of acetic acid, and 50 ml of methanol are heated at reflux for 5 hr, and allowed to stand at room temperature overnight. The mixture is then heated at reflux for an additional 2 hr, cooled, and concentrated to dryness in vacuo. The residue is treated with 7 ml of 50% acetic acid. The precipitate is collected, washed with cold 50% acetic acid, crystallized from benzene, and recrystallized from ethanol:water, to yield 23.9 g (35%) of the titled crystals, having a melting point of 220°–221° C. The C:H:N ratio is 58.45:2.59:3.52.

EXAMPLE 30

2-(4-Bromophenyl)-6-(4-chlorophenyl)-4-pyridinecarboxylic acid (Formula II: $X_{20}$ is bromo, $X_{30}$ is chloro, $R_{10}$, $R_{20}$, $X_{10}$, $X_{40}$, and $X_{50}$ are hydrogen)

Following the procedure of the preceding examples, the titled crystals are prepared and are recrystallized from acetic acid:water in a 45.9% yield, having a melting point of 290°–292° C. with a C:H:N ratio of 55.32:2.79:3.57.

EXAMPLE 31

1-(4-Chlorophenyl)-6-[4-(trifluoromethyl)phenyl]-4-pyridinecarboxylic acid (Formula II: $X_{20}$ is trifluoromethyl, $X_{30}$ is chloro, $X_{10}$, $X_{40}$, $X_{50}$, $R_{10}$ and $R_{20}$ are hydrogen)

Following the procedure of the preceding examples, the titled crystals are obtained in 79% yield from acetic acid:water. These crystals have a melting point of 268°–270° C. The C:H:N ratio is 60.08:2.79:3.82.

EXAMPLE 32

2,6-bis[4-(Trifluoromethyl)phenyl]-4-pyridinecarboxylic acid (Formula II: $X_{20}$ and $X_{30}$ are trifluoromethyl, $X_{10}$, $X_{40}$, $X_{50}$, $R_{10}$ and $R_{20}$ are hydrogen)

Following the procedures of the preceding examples, the titled crystals are obtained from ethanol:water with a melting point of 289°–290° C. and the C:H:N ratio of 57.56:3.94:3.48.

EXAMPLE 33

2,6-bis(4-Bromophenyl)-4-pyridinecarboxylic acid (Formula II: $X_{20}$ and $X_{30}$ are bromo, $X_{10}$, $X_{40}$, $X_{50}$, $R_{10}$, and $R_{20}$ are hydrogen)

Following the procedure of the preceding examples, the titled crystals are obtained in 57% yield from ethanol, having a melting point of 292°–294° C. in a C:H:N ratio of 49.10:2.79:4.35.

EXAMPLE 34

2-(4-Chlorophenyl)-6-(3,4-dichlorophenyl)-4-pyridinecarboxylic acid (Formula II: $X_{10}$, $X_{20}$, and $X_{30}$ are chloro, $X_{40}$, $X_{50}$, $R_{10}$, and $R_{20}$ are hydrogen)

Following the procedure of the preceding examples, the titled crystals are obtained from acetonitrile in 28% yield having a melting point of 303°–304° C. and a C:H:N ratio of 56.20:2.64:3.86.

EXAMPLE 35

Ten thousand hard gelatin capsules for oral use, each containing 25 mg of 2,6-bis(4-Chlorophenyl)-4-pyridine carboxylic acid and 2.5 mg of minoxidil are prepared from the following ingredients:

|  | Gm. |
|---|---|
| 2,6-bis(4-Chlorophenyl)-4-pyridinecarboxylic acid | 250 |
| Minoxidil | 25 |
| Starch | 350 |
| Talc | 250 |
| Calcium stearate | 150 |
| Lactose | 1750 |

One capsule one to 4 times a day is useful in the treatment of hypertension.

EXAMPLE 36

Ten thousand tablets for oral use, each containing 25 mg of 2,6-bis(4-chlorophenyl)-4-pyridine carboxylic acid are prepared from the following ingredients:

|  | Gm. |
|---|---|
| 2,6-bis(4-Chlorophenyl)-4-pyridinecarboxylic acid | 250 |
| Lactose | 1200 |
| Corn starch | 500 |
| Talc | 500 |
| Calcium stearate | 25 |

The powdered ingredients are thoroughly mixed and slugged. The slugs are broken into granules which are then compressed into tablets. To induce diuresis in adult humans, 1 tablet is administered 1 to 4 times daily.

EXAMPLE 37

Following the procedures of the preceding Examples, and the procedures given in the Markovac, LaMontagne, and Blumbergs references and U.S. Pat. Nos. 3,753,997, 3,763,148, and 3,600,396, all of the remaining compounds within the scope of this invention are prepared.

FORMULAS

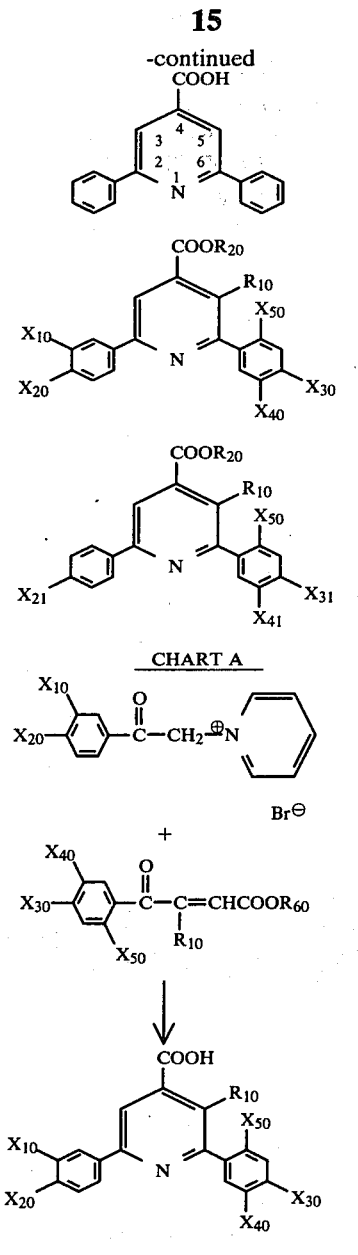

CHART A

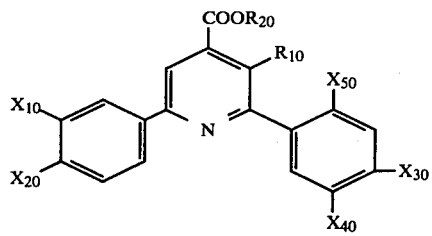

I claim:
1. A method for inducing diuresis in a human in need of such treatment which comprises systemically administering to said human an amount effective to cause diuresis of a compound of the Formula II, wherein
(1) $R_{10}$ is hydrogen or methyl;
(2) $R_{20}$ is hydrogen or a pharmacologically acceptable cation;
(3) $X_{10}$ is hydrogen or trifluoromethyl;
(4) $X_{20}$ is hydrogen, chloro, fluoro, bromo, iodo, or trifluoromethyl;
(5) $X_{30}$ is hydrogen, methyl, chloro, bromo, iodo, trifluoromethyl, or —CH$_2$—R$_{50}$, wherein R$_{50}$ is (C$_2$–C$_7$) alkyl;
(6) $X_{40}$ is hydrogen, chloro, fluoro, trifluoromethyl, or methyl; and
(7) $X_{50}$ is hydrogen, (C$_1$–C$_4$) alkoxy or acetoxy;
with the following provisos:
(a) at least one of $X_{10}$ and $X_{20}$ and at least one of $X_{30}$ and $X_{40}$ is other than hydrogen;
(b) $X_{10}$ is trifluoromethyl only when $X_{20}$ is hydrogen, $X_{30}$ is hydrogen, and $X_{40}$ is trifluoromethyl;
(c) $X_{40}$ is chloro only when $X_{30}$ is chloro;
(d) one of $X_{30}$ and $X_{40}$ is methyl only when the other is methyl;
(e) $X_{50}$ is (C$_1$–C$_4$) alkoxy or acetoxy only when $X_{10}$ and $X_{40}$ are hydrogen, $X_{20}$ is chloro, bromo, iodo, or trifluoromethyl, and $X_{30}$ is chloro, bromo, iodo, trifluoromethyl, or CH$_2$—R$_{50}$;
(f) $X_{20}$ is fluoro only when $R_{10}$ is methyl and $X_{30}$ is chloro; and
(g) $X_{40}$ is fluoro only when $X_{30}$ is phenyl.

2. A method of claim 1 wherein the compound of the Formula II is selected from the group consisting of
2-(4-chlorophenyl)-6-[3-(trifluoromethyl)phenyl]-4-pyridinecarboxylic acid,
2-(4-bromophenyl)-6-[3-(trifluoromethyl)phenyl]-4-pyridinecarboxylic acid,
2-(4-chlorophenyl)-6-(3,4-dimethylphenyl)-4-pyridinecarboxylic acid,
2,6-bis(4-chlorophenyl)-3-methyl-4pyridinecarboxylic acid,
2-(4-chlorophenyl)-6-(4-iodophenyl)-4-pyridinecarboxylic acid,
2-(4-chlorophenyl)-6-(4-propylphenyl)-4-pyridinecarboxylic acid,
2-(4-chlorophenyl)-6-(4-phenoxyphenyl-4-pyridinecarboxylic acid,
2-(4-chlorophenyl)-6-[4-(2-methylpropyl)phenyl]-4-pyridinecarboxylic acid,
2-(4-butylphenyl)-6-(4-chlorophenyl)-4-pyridinecarboxylic acid,
2-(4-chlorophenyl)-6-[4-(3-methylbutyl)phenyl]-4-pyridinecarboxylic acid,
2-(4-chloro-2-methoxyphenyl)-6-(4-chlorophenyl)-4-pyridinecarboxylic acid,
2-[2-(acetyloxy)-4-chlorophenyl]-6-(4-chlorophenyl)-4-pyridinecarboxylic acid,
2-(4-chlorophenyl)-6-(4-fluorophenyl)-3-methyl-4-pyridinecarboxylic acid,
2-(4-bromophenyl)-6-(4-chlorophenyl)-5-methyl-4-pyridinecarboxylic acid,
2,6-bis(4-chlorophenyl)-4-pyridinecarboxylic acid,
2,6-bis(4-chlorophenyl)-4-pyridine carboxylic acid, sodium salt hydrate,
2,6-bis[(3-trifluoromethyl)phenyl]-4-pyridinecarboxylic acid,
2-(4-bromophenyl)-6-(4-chlorophenyl)-4-pyridine carboxylic acid,
1-(4-chlorophenyl)-6-[4-(trifluoromethyl)phenyl]-4-pyridinecarboxylic acid,
2,6-bis[4-(trifluoromethyl)-phenyl]-4-pyridine carboxylic acid,
2,6-bis(4-bromophenyl)-4-pyridine carboxylic acid,
2-(4-chlorophenyl)-6-(3,4-dichlorophenyl)-4-pyridinecarboxylic acid, and
2,6-Bis(4-chlorophenyl)-3-methyl-4-pyridinecarboxylic acid.

3. A method of claim 2, wherein the compound of the Formula II is 2,6-bis-(4-chlorophenyl)-4-pyridinecarboxylic acid, or its sodium salt.

* * * * *

UNITED STATES PATENT OFFICE
CERTIFICATE OF CORRECTION

Patent No. 4,377,586     Dated  22 March 1983

Inventor(s) L.L. Skaletzky

It is certified that error appears in the above-identified patent and that said Letters Patent are hereby corrected as shown below:

Column 1, line 19, "purposes" should read -- purpose --.
Column 7, line 50, "71.54:" should read -- 71.53: --.
Column 13, line 33, "23.9 g" should read -- 2.3 g --.

Signed and Sealed this

Seventeenth Day of May 1983

[SEAL]

Attest:

DONALD J. QUIGG

Attesting Officer     Acting Commissioner of Patents and Trademarks